United States Patent [19]

Kent

[11] Patent Number: 4,839,456

[45] Date of Patent: Jun. 13, 1989

[54] SELF-ADHESIVE, DRAG REDUCING POLYMERIC COATING

[76] Inventor: Keith Kent, 12515 Sugar Pine Way, Tampa, Fla. 33624

[21] Appl. No.: 784,218

[22] Filed: Oct. 4, 1985

Related U.S. Application Data

[63] Continuation-in-part of Ser. No. 512,872, Jul. 12, 1983, Pat. No. 4,623,593.

[51] Int. Cl.$^4$ .............................................. C08G 77/04
[52] U.S. Cl. .......................................... 528/33; 528/18
[58] Field of Search ........................... 528/18, 33, 283; 526/82, 192

[56] References Cited

U.S. PATENT DOCUMENTS

| | | | |
|---|---|---|---|
| 2,692,873 | 10/1954 | Langerak et al. | 260/77.5 |
| 3,179,625 | 4/1965 | Ehrhart | 260/75 |
| 3,300,542 | 1/1967 | Hadlock | 528/33 |
| 3,352,829 | 11/1967 | Blomeyer et al. | 260/77.5 |
| 3,483,167 | 12/1969 | Sommer et al. | 260/75 |
| 3,532,649 | 10/1970 | Smith et al. | 528/18 |
| 3,607,801 | 9/1971 | Fulton | 528/18 |
| 3,624,022 | 11/1971 | Ross | 528/18 |
| 3,635,907 | 1/1972 | Schulze et al. | 260/77.5 |
| 3,819,553 | 6/1974 | Stephens et al. | 260/28 |
| 3,865,759 | 2/1975 | Smith | 528/18 |
| 4,026,875 | 5/1977 | Leu et al. | 260/77.5 |
| 4,081,429 | 3/1978 | Wyman et al. | 260/77.5 |
| 4,158,027 | 6/1979 | Restaino | 260/859 |
| 4,251,596 | 2/1981 | de Montgny et al. | 528/33 |
| 4,410,677 | 10/1983 | Lampe | 528/33 |
| 4,443,502 | 4/1984 | Gutek | 528/33 |
| 4,574,793 | 3/1986 | Lee et al. | 128/90 |
| 4,623,593 | 11/1986 | Baier et al. | 528/17 |
| 4,624,014 | 11/1971 | Moore et al. | 528/18 |

*Primary Examiner*—Harold D. Anderson
*Assistant Examiner*—Dennis R. Daley
*Attorney, Agent, or Firm*—Herbert L. Bello

[57] ABSTRACT

A self-adhering polymeric composition for use as a drag-reducing fouling-release coating and a method for making such composition. The composition, which is formed by mixing a base polymer with a curing catalyst and immediately adding trace amounts of a inhibitor modifier to the mixture, produces a high integrity coating with a surface extended network of differentially cross-linked chains that reach into and control the flow-/adhesion properties in the liquid phase.

9 Claims, No Drawings

SELF-ADHESIVE, DRAG REDUCING POLYMERIC COATING

CROSS-REFERENCE TO RELATED APPLICATIONS

This is a continuation-in-part of Ser. No. 512,872, filed July 12, 1983, now U.S. Pat. No. 4,623,593.

BACKGROUND OF THE INVENTION

The present invention relates to polymeric compositions and, more particularly, if directed towards self-adhering polymeric composition for use as a drag reducing coating.

Various coatings have been developed for reducing drag between two surfaces in relative motion. For example, U.S. Pat. No. 2,937,976 discloses a drag reducing gel for a razor blade and U.S. Pat. No. 4,385,134 teaches use of a drag reducing, antifouling coating for boat hulls.

The primary cause of drag on boat hulls is the growth of marine organisms on the hull. Generally, antiflouling coatings contain a toxicant agent which controls the growth of marine organisms. In such coatings it is necessary to control the amount of toxin delivered to the surface coating in order to prevent premature depletion of the antifouling agent. Other patents relating to drag reducing compositions for boat hulls include U.S. Pat. Nos. 3,575,123; 3,896,753; and 3,990,381. A need has arisen for an improved drag reducing coating for marine use which does not require use of a toxicant agent.

Also, there is a need for drag reducing composition which can be readily manufactured in form which can be easily applied to the surface of the object to be protected. Such a drag reducing composition should ideally be paintable or sprayable on the object surface and act to protect the underlying surface from degradation by bacterial decay, oxidation, water seepage and the like. Once such a drag reduction and/or protective coating is applied to an object surface, the coating should readily adhere to the surface, remain in such adherence, and itself be relatively inert to ambient sources of degradation.

SUMMARY OF THE INVENTION

In accordance with the invention there is provided a mothod for producing a polymeric composition comprising the steps of: bulk mixing a base polymer forming material with a catalyst; immediately adding trace amounts of a cross-linking inhibitor to the bulk mixture; and curing and polymerizing the inhibited bulk mixture.

The base polymer forming material preferably includes one or more of a monomer unit of a polymer, a prepolymer of polymer, or an unvulcanized form of the polymer which is preferably selected from the group of silicones, polyrethanes, polyacrylics, polyesters, polyolefins, polyacrylamides and polyether-urethane polymers.

There is also provided a method for producing a drag reducing polymer composition comprising the steps of: selecting a base compound comprising polymer forming units bulk mixing the base compound with a catalyst in an amount sufficient to polymerize essentially all of the polymer forming units; and adding a cross linking inhibition agent to the bulk mixture. In one example, the cross linking inhibition agent is added immediately after the step of bulk mixing is carried out. The cross-linking inhibition agent is preferably added in an amount sufficient to inhibit cross-linking to a predetermined degree. The mixture is typically subjected to polymerization conditions, such as heating, mixing, solution in solvent and the like, for a predetermined amount of time sufficient to effect predetermined amount of polymerization and cross-linking.

The base compound typically includes unvulcanized silicon based polymers, and the inhibition agent is preferably added in a trace amount. The mixture of polymer forming material may be allowed to begin polymerizing, but only a slight degree, before the inhibition agent is added.

In accordance with the invention there is also provided a blend of one or more of a selected monomer, a prepolymer of the monomer, and a polymer of the monomer; a catalyst for causing unpolymerized components of the blend to polymerize and cross-link with the catalyst being added to the blend in an amount sufficient to polymerize and cross-link essentially all of the unpolymerized components of the blend; and a trace amount of a modifier which inhibits cross-linking, wherein, in one embodiment, the modifier is added to the blend and the catalyst essentially immediately after the blend. The monomer preferably comprises a monomer unit of one or more of a silicone, polyurethane, acrylic, polyester, polyolefin, polycrylamide or polyether-urethane copolymer.

An integral surface layer having pressure-sensitive adhesive properties may be formed on an otherwise fully cured polymeric body by applying a sufficient amount of a cross-linking inhibition agent to selected surfaces of a mold cavity prior to packing the cavity with uncured monomeric, prepolymeric, or unvulcanized polymeric material. The mold is then closed and the material cured. The cross-linking inhibition agent acts on the surface or surfaces of the polymer to prevent complete cross-linking thereof. The body of the polymer is otherwise completely cured and has the same properties as would be expected of a fully polymerized and cross-linked composition. Conventional additives such as fibers and fillers may be added to the uncured compound and have no effect on the integral surface layer which is formed. In applications where selected surfaces of a polymerized body are treated with inhibition agent, the surface or surfaces of the polymeric body which are cured in contact with the cross-linking inhibition agent remain tacky and possess pressure sensitive adhesive properties. The present invention deals with treatment of the bulk prepolymer rather then treatment of selected surfaces of the prepolymer.

Accordingly, it is an object of the present invention to provide a self-adhering polymeric composition for use as a drag reducing coating. Self-adhering as used in this application means that the composition will adhere to a surface to be coated without special treatment of the surface.

It is another object of the present invention to provide a self-adhering polymeric composition for use as a fouling release, drag reducing coating.

It is a further object of the invention to provide a method for forming a self-adhering composition for use as a drag reducing coating. The coating is produced by inhibiting and permanently arresting the process of curing of a polymer. The method of forming the polymeric composition includes the steps of mixing a base polymer with a catalyst, and adding trace amounts of a modifier to the mixture. Preferably, the resultant composition is heated to accelerate the polymerization process. The resulting composition is a high integrity coating with all the useful engineering features of the bulk polymer with a surface network of differential cross-linked chains that reach into and control the flow/adhesion properties in the liquid phase.

Other objects, features and advantages will be apparent from the following detailed description of preferred embodiments:

DESCRIPTION OF PREFERRED EMBODIMENTS

The drag reducing polymer composition of the invention may be produced from a base polymer composition any one or more of a selected unvulcanized polymer, a prepolymer thereof, a monomer unit of the selected polymer or a mixture of one or more or all of the foregoing. The polymers, prepolymers thereof and monomer units of such polymers preferred for use in producing the drag reducing composition include silicones, polyurethanes, polyacrylics, polyesters, polyolefins, polyacrylamides and polyetherurethane copolymers. The polymers presently preferred in the practice of the present invention are silicone elastomers and specifically polydimethylsiloxanes because of their ready availability.

The base polymer composition is mixed in bulk with a catalyst which catalyzes both straight chain polymerizaton and cross-linking. The catalyst selected is typically peculiar to catalysis of the selected monomer units of the polymers to be formed, and is preferably added in an amount sufficient to polymerize and/or cross-link essentially all of the polymer forming material of the base polymer composition. In the case, for example, where a silicone polymer composition is to be formed, the selected base polymer composition including catalyst may comprise one or more MDX-4-4210, SILGARD 194, AND SILGARD 196 silicone prepolymers commercially available from the Dow Corning Corp., GTE RTVII, a prepolymer commercially available from the General Electric Co. In the case of MDX-4-4210, one part of the catalyst is mixed with each ten parts by weight of the base material. The catalysts employed for polymerization of such base compositions, catalyze a condensation reaction between the silicon elements which are typically bonded to one or more hydroxy or halogeno elements.

When the catalyst and base polymer forming units are mixed in bulk, a modifier, typically an inhibition agent, is added to the mixture. Preferably, the modifier is added to the mixture essentially immediately after the mixing of the catalyst and base polymer forming units. In one example, trace amounts of an inhibitor is added to the bulk mixture of the base polymer and catalyst. Where silicone prepolymer compositions are employed, the process is most preferably assisted by heating the base polymer/catalyst/modifier mixture to at least about 100 degrees Centigrade for at least about 20 minutes. Preferred modifiers, which are imcompatible with the normal polymerization process and permanently inhibit and arrest polymerization before it is completed, include metals salts of carboxylic acids, most preferably stannous octoate.

The consistency of the drag reducing polymer composition may be controlled by controlling the degree of polymerization. The degree of polymerization may be controlled by accelerating or decelerating the conditions favoring polymerization such as by increasing or decreasing temperature for longer or shorter periods of time, allowing the base composition to begin polymerization to some predetermined degree before adding an inhibition agent, increasing or decreasing the amount of catalyst and the like.

The resulting drag reducing composition may range in consistency from a wax-like substance to a runny liquid depending upon the predetermined degree of polymerization allowed. Preferably the composition is produced in such a consistency that the resulting mixture may be directly painted on the surface of an object to be protected. Notwithstanding the physical consistency of the resulting mixture, the mixture may be thinned, i.e., dissolved, in conventional organic solvents such as fluorocarbons, hydrocarbons, ethers, ketones and the like, to any predetermined degree to aid in the ready application of the resulting drag reducing polymer composition. In any event, once the composition is inhibited, polymerization is permanently arrested. Application of additional catalysts, heat or other standard modalities will not cause further vulcanization of the composition.

Without wishing to be limited to any specific theory or mechanism, we believe that the application of certain agents, which we will term permanent cross-linking inhibition agents, will permanently inhibit the degree of cross-linking of the polymeric composition which occurs during a curing or vulcanization step. This results in a multiplicity of elastomeric polymer chains. Several suitable cross-linking inhibition agents specific to prepolymers such as MDX4-4210 include metal salts of carboxylic acids such as stannous octoate. Prepolymers such as MDX4-4210; SILGARD 184 and 186; and SILASTIC 31-10, 31-12 and 31-20 are compatable with inhibitors such as chlorinated and butyl rubbers; most other room temperature vulcanizing (RTV) silicone rubbers; sulphur containing solvents; plasticizers; and tin containing compounds. Prepolymer such as SILASTIC 382, General Electric RTV-11 are compatable with inhibitors such as oxidizing oils; linseed oils; putties; oil containing clays; and plastizers, specifically amine containing plasticizers. Those skilled in the art may determine other suitable cross-linking inhibition agents by simple testing.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. A method for producing a drag reducing polymeric composition comprising the steps of:

mixing a silicone polymer with a catalyst, the quantity of catalyst being sufficient to polymerize essentially all of said silicone polymer;

immediately adding a cross-linking inhibitor which is an inhibitor for said silicone polymer and inhibits the resulting silicone polymer mixture and permanently arrests polymerization; and polymerizing the resulting inhibited silicone polymer mixture to form a drag reducing polymeric composition, the consistency of the resulting drag reducing polymeric composition is in the range of a wax-like substance to a running liquid even when the resulting polymeric composition is subjected to a temperature of 100° C. for twenty minutes.

2. The product of the method carried out according to claim 1.

3. A method for producing a drag reducing polymeric composition comprising the steps of:
   selecting a base silicone polymer;
   bulk mixing the base silicone polymer with a catalyst in an amount sufficient to polymerize essentially all of the polymer forming units; and
   adding a cross-linking inhibitor which is an inhibitor for said base silicone polymer, said inhibitor inhibits the resulting bulk mixture and permanently arrests the complete cure of the polymer so as to result in a drag reducing polymeric composition having a consistency ranging from a wax-like substance to a running liquid even when the resulting polymeric composition is subject to a temperature of 100° C. for twenty minutes.

4. A drag reducing polymeric composition comprising:
   (a) a base silicone polymer having unpolymerized components;
   (b) a catalyst for causing said unpolymerized components of said base silicone polymer to polymerize and cross-link, said catalyst added to said base silicone polymer in an amount sufficient to polymerize and cross-link essentially all of said unpolymerized components of said base silicone polymer; and
   (c) an inhibitor for said base silicone polymer, said inhibitor inhibits cross-linking, said inhibitor being in sufficient quantity to inhibit and permanently arrest complete curing of said base silicone polymer and catalyst and result in a drag reducing polymeric composition, the consistency of said drag reducing polymeric composition being controlled by controlling the degree of polymerization, said consistency ranging from a wax-like substance to a running liquid even when the polymeric composition is subjected to a temperature of 100° C. for a period of twenty minutes.

5. The method of claim 4 wherein the silicone base compound further comprises unvulcanized silicon based polymers.

6. The method of claim 5 wherein the inhibition agent is selected from the group consisting of metal salts of carboxylic acids.

7. The method of claim 3 wherein the step of bulk mixing comprises allowing the base compound to begin polymerizing before the inhibition agent is added.

8. A drag reducing polymeric composition comprising:
   a silicone polymer having unpolymerized components;
   a catalyst for causing said unpolymerized components of said silicone polymer to polymerize and cross-link, said catalyst added to said silicone polymer in an amount sufficient to polymerize and cross-link essentially all of said unpolymerized components of the resulting polymeric mixture; and
   an inhibitor for said silicone polymer, said inhibitor inhibits cross-linking, said inhibitor is added to said resulting polymeric mixture essentially immediately after said silicone polymer and said catalyst are intermixed, said inhibitor inhibiting said resulting polymeric mixture and permanently arresting polymerization to form a drag reducing polymeric composition, the consistency of said polymeric composition being controlled by controlling the degree of polymerization, said consistency ranging from a wax-like substance to a running liquid even when said resulting polymeric composition is subjected to a temperature of 100° for a period of twenty minutes.

9. The composition of claim 8 wherein the modifier is selected from the group of inhibitors consisting of cyanoacrylates and metals salts of carboxylic acids.

* * * * *